United States Patent
Albrektsson et al.

[11] Patent Number: 5,997,579
[45] Date of Patent: Dec. 7, 1999

[54] LINER

[75] Inventors: Björn Albrektsson, Onsala; Lars Carlsson, Kullavik; Magnus Jacobsson, Göteborg; Tord Röstlund, Kullavik; Stig Wennberg, Angered, all of Sweden

[73] Assignee: Astra Aktiebolag, Sodertalje, Sweden

[21] Appl. No.: 08/553,522

[22] PCT Filed: Oct. 27, 1995

[86] PCT No.: PCT/SE95/01274

§ 371 Date: Nov. 15, 1995

§ 102(e) Date: Nov. 15, 1995

[87] PCT Pub. No.: WO96/13231

PCT Pub. Date: May 9, 1996

[30] Foreign Application Priority Data

Oct. 28, 1994 [SE] Sweden ................................ 9403699

[51] Int. Cl.⁶ .................................................. A61F 2/34
[52] U.S. Cl. .................................................. 623/22
[58] Field of Search ........................... 623/16, 18, 22, 623/23

[56] References Cited

U.S. PATENT DOCUMENTS

| | | |
|---|---|---|
| 3,818,512 | 6/1974 | Shersher . |
| 4,135,517 | 1/1979 | Reale . |
| 4,241,463 | 12/1980 | Khovaylo . |
| 4,650,491 | 3/1987 | Parchinski ................................ 623/22 |
| 4,743,262 | 5/1988 | Tronzo ...................................... 623/22 |
| 4,822,367 | 4/1989 | Stuhmer .................................... 623/22 |
| 4,834,759 | 5/1989 | Spotorno et al. ......................... 623/22 |

FOREIGN PATENT DOCUMENTS

| | | |
|---|---|---|
| 0256740 | 2/1988 | European Pat. Off. . |
| 2626168 | 7/1989 | France . |
| 2628314 | 9/1989 | France . |

*Primary Examiner*—David J. Isabella
*Attorney, Agent, or Firm*—White & Case LLP

[57] ABSTRACT

The present invention relates to a cup-shaped member for a hip joint prosthesis for implantation into a cavity in the bone tissue in the acetabulum, and more particularly to an acetabular cup-liner assembly, in which the acetabular cup has an outer surface intended to face the bone tissue in the acetabulum and an inner surface intended to face a liner. The liner has an outer surface intended to face the inner surface of the cup, and the cup is provided with an opening adapted to receive the liner. At least the parts of the liner corresponding to the parallel inside walls of the cup have dimensions equal to or a fraction less than the inner dimensions of the sidewalls. The parts of the surfaces of the inner side walls of the cup located adjacent to the opening of the cup are essentially parallel to each other. The surface of at least the parallel inner side walls of the cup is provided with a grooved region. The liner has an outer shape that is complementary to the inner shape of the cup. The parts of the liner corresponding to the parallel inside walls of the cup are provided with a grooved region corresponding to said grooved region on said cup.

14 Claims, 3 Drawing Sheets

LINER

TECHNICAL FIELD OF THE INVENTION

The present invention relates to a cup-shaped member for a hip joint prosthesis for implantation into a cavity in the bone tissue in the acetabulum, and more particularly to an acetabular cup-liner assembly, i.e. an assembly comprising an acetabular cup together with a liner for said cup, in which the acetabular cup has an outer surface intended to face the bone tissue in the acetabulum and an inner surface intended to face said liner, said liner preferably being made of UHMWPE (Ultra High Molecular Weight Polyethylene) and said cup preferably being made of titanium, said liner having an outer surface intended to face the inner surface of the cup, said cup being provided with an opening adapted to receive said liner.

The invention further relates to methods of manufacturing an acetabular cup and a liner for an acetabular cup.

BACKGROUND TO THE INVENTION

Artificial hip joints have been used and implanted into humans for a long period of time. The joints normally comprise one femoral part which is intended to be inserted or implanted into the femur and which carries a ball-shaped articulation element, normally made of metal or a ceramic material. The joint further normally comprises a cup-shaped member, i.e. an acetabular cup, which is to be inserted into or attached to the acetabulum, and which is to hold a complementary, cup-shaped liner, normally made of Ultra High Molecular Weight Polyethylene (UHMWPE) or an alternative bearing or wear material, in which the ball-shaped element is to articulate or rotate.

Since the depth of the bone tissue which is available in the acetabulum for attaching the acetabular cup is limited, the possibilities of varying the design of the acetabular cup are rather restricted, which poses similar restrictions on the liner. One result of the lack of bone tissue in the acetabulum is that a typical acetabular cup is rather shallow. This fact makes it rather difficult to find a simple and efficient design and method for attaching a liner into an acetabular cup in a firm and secure manner.

The designs and methods used today mostly utilize circumferential beads or spring wires engaging a complementary groove or other snap action means as means for locking a liner in an acetabular cup. These features normally are complemented with anti-rotation means such as anti-rotation lugs etc. preventing the liner from rotating in the cup. In addition, micromovements still occur which may result in wear and debris production.

Some examples of prior designs according to these principles are disclosed in U.S. Pat. Nos. 3,903,549, 4,795,470 and 5,049,158.

These designs have the disadvantage that they are relatively difficult to make and also to use, since separate locking rings or wires as well as relatively large locking beads or grooves might present difficulties when the liner is to be inserted into the cup during an operation in view of the inherent rigidity of the polymer material serving as bearing or wear material in conjunction with the relatively large deformation necessary.

FR-A-2626168 (G. Cremascoli S.P.A.) discloses a modular hip prosthesis including a cup and a polyethylene element comprising a part manufactured in the shape of a spherical skullcap and an slightly conical annular part. The connection between these is strengthened by the presence of a series of indentations formed on the circumference of the cup in planes parallel to the one defining the opening of the cup.

In practice, the conicity of said annular part is said to allow a stable and perfect connection to be maintained between the exterior titanium surface and the interior polyethylene element. The cup is rendered elastic through the provision of a series of radial slits.

We have observed a disadvantage of making the annular part conical in that the titanium ball might cause impingement on the interior polyethylene element. The radial slits are also disadvantageous in that many surfaces are generated during their manufacture. This can cause the generation of wear particles between the elements, resulting in the dispersal of polyethylene particles through organic tissue and possible bone breakdown.

DISCLOSURE OF THE INVENTION

We have now found that the above disadvantages may be eliminated by using a cup in which the parts of the surfaces of the inner side walls of said cup located adjacent to the opening of said cup are essentially parallel to each other and the surface of said parallel inner side walls of said cup is provided with a preformed grooved region; and a liner in which the parts of the liner corresponding to the parallel inside walls of said cup are also provided with a preformed grooved region corresponding to said grooved region on said cup.

Thus, according to the present invention we provide an acetabular cup-liner assembly, in which the acetabular cup has an outer surface intended to face the bone tissue in the acetabulum and an inner surface intended to face said liner, said liner having an outer surface intended to face the inner surface of the cup, said cup being provided with an opening adapted to receive said liner, said liner having an outer shape which is complementary to the inner shape of the cup and at least the parts of the liner corresponding to the inside walls of said cup having dimensions being equal to or a fraction less than the inner dimensions of said sidewalls, whereby the cup-liner assembly may be assembled by translational movement of the liner relative to the cup, characterized in that the parts of the surfaces of the inner side walls of said cup located adjacent to said opening of said cup are essentially parallel to each other;

the surface of said parallel inner side walls of said cup is provided with a preformed grooved region; and said parts of the liner corresponding to said parallel inside walls of said cup are also provided with a preformed grooved region corresponding to said grooved region on said cup.

The invention gives an acetabular cup-liner assembly which is easy to make and in which the liner is easy to mount, also during surgery, the liner being seated firmly in the acetabular cup after mounting.

The inner, opposing side walls of said cup are preferably in the form of an inner circular cylindrical surface adjacent to the opening of said cup. This ensures ease of manufacture and fit compared with, say, elliptical cylindrical surfaces. Although badly formed conical surfaces may be easier to fit together than badly formed cylindrical surfaces, making the tolerance stricter ensures that this problem is not in fact encountered with cylindrical surfaces.

With obliquely oriented grooves, dislocation might occur. Thus, preferably the grooved region on the cup comprises a circumferentially oriented series of grooves or one or more helical grooves located on said inner cylindrical surface of said cup.

If the grooved region were at the open end of the cup, any cut-outs at this end of the cup or liner would interfere with their action, as at least one grooved region would be interrupted. Thus, preferably the grooved region is located in the central part of the cylindrical surface, leaving a smooth, cylindrical part on each side of said grooved region. This also has the advantage that, if the components tilt, relative movement is still prevented, whereas if they were at either end they could come apart. The flat surfaces allow a 'drawer' effect to be manifest.

The grooved region could be cast, but casting titanium is difficult with known methods. Precision would be difficult with casting, and there could be a problem with undercuts, which are difficult to remove. Thus, preferably the grooved region on the cup comprises one or more grooves obtained by scoring the surface in a turning operation. This ensures ease of manufacture.

The depth (h) of the grooves on the cup is preferably between 0.020 and 0.30 mm, and the distance (d) between adjacent grooves is preferably between 0.12 and 0.2 mm. In the case of there being a single helical groove, it will be understood that the distance (d) refers to the distance between adjacent portions of the groove.

The assembly works most efficiently if the grooved region on the liner is opposite that on the cup. Thus, preferably the liner is provided with a cylindrical part located on said liner to coincide with said cylindrical part in said cup when said liner is located in said cup, said grooved region being located on said cylindrical part of said liner to at least partly coincide with said grooved region on the cup.

The grooved region on the liner will define a series of circumferential beads or one or more helical beads between them, the beads being separated by the grooves or cuts. Preferably the grooved region on the liner defines a series of beads having a height of about 0.08–1.0 mm as counted from the cylindrical surface of the liner. More preferably, the beads may have a height of 0.1–0.7 mm, a height of 0.1–0.5 mm, a height of 0.1–0.2 mm, or most preferably a height of 0.1–0.14 mm.

Dislocation might also occur if the cap and liner were provided with slits as disclosed in FR-A-2626168 (G. Cremascoli S.P.A). Thus, preferably the cup and liner are substantially free of slits extending through from one surface to the other.

Any materials may be used, but preferably the cup is made of titanium and the liner is made of UHMWPE (Ultra High Molecular Weight Polyethylene).

In a further aspect of the invention we provide a method for providing a liner and an acetabular cup with a grooved region comprising a circumferentially oriented series of grooves or one or more helical grooves on the surface of the cylindrical inside of an acetabular cup for use in such an assembly, characterized in that said surface is scored in a turning operation.

The scoring is ideally performed with a tool having a specified tip radius and with a specified feed. The tool may have a tip radius (r) of 0.1 mm, the feed (d) being 0.15 mm, resulting in a depth (h) of the scores of 0.025 mm.

We also provide a method for providing the outside cylindrical side walls of a liner for an acetabular cup according to with a grooved region comprising a circumferentially oriented series of grooves or one or more helical grooves, characterized in that grooves are cut into the cylindrical outer surface of the liner with a sharp-edged tool, preferably in a turning operation.

Said grooves are preferably cut to a depth of about 0.5 the distance between each groove being about 0.3 or 0.4 mm.

SHORT DESCRIPTION OF THE APPENDED DRAWINGS

A preferred embodiment of the invention will now be described, by way of example, with reference to the accompanying drawings, in which FIG. 1 illustrates an acetabular cup according to the invention in elevation, FIG. 2 is a side view of the cup in FIG. 1, FIG. 3 is a section along the line III—III in FIG. 1, FIG. 4 illustrates a preferred embodiment of the grooved region in the inside of the side walls of the cup, FIG. 5 is a perspective view of a liner according to the invention, FIG. 6 is an elevational view of a liner according to the invention, FIG. 7 is a side view of the liner in FIG. 6, FIG. 8 is another side view of the liner in FIG. 6, FIG. 9 is a section of the liner taken along the line IX—IX in FIG. 6, FIG. 10 illustrates a preferred embodiment of the rough surface on the outside of the side walls of the liner, and FIG. 11 illustrates a method of providing the rough surface in FIG. 10 on the outside of the liner.

DETAILED DESCRIPTION OF A PREFERRED EMBODIMENT OF THE INVENTION

Figure 1:
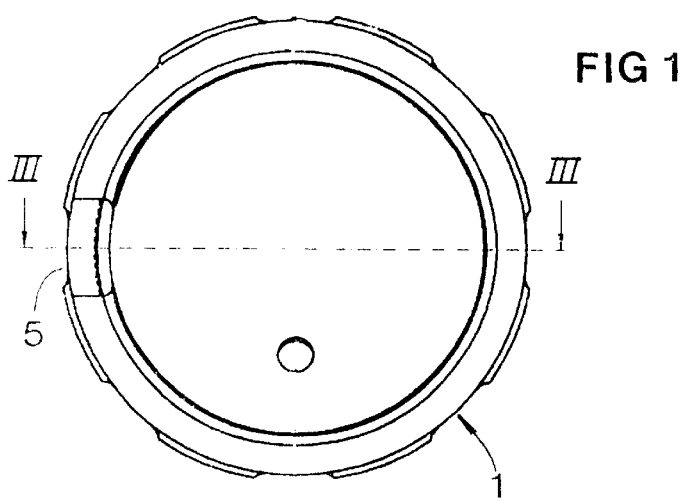
Figure 2:
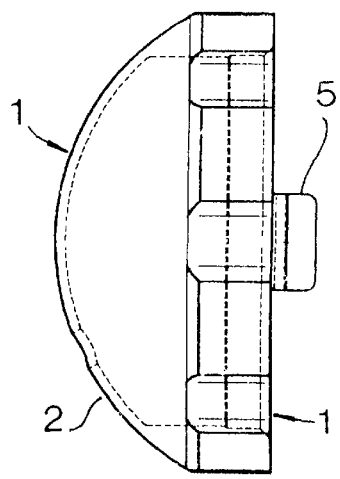
Figure 3:
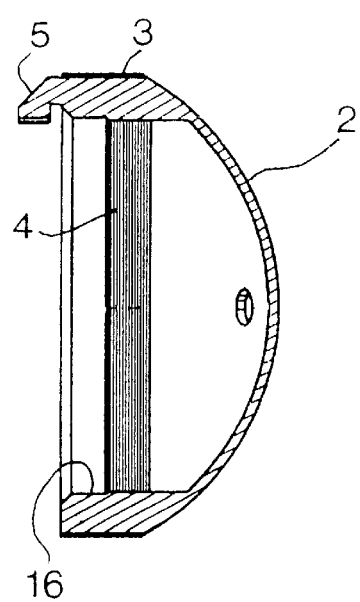
Figure 4:
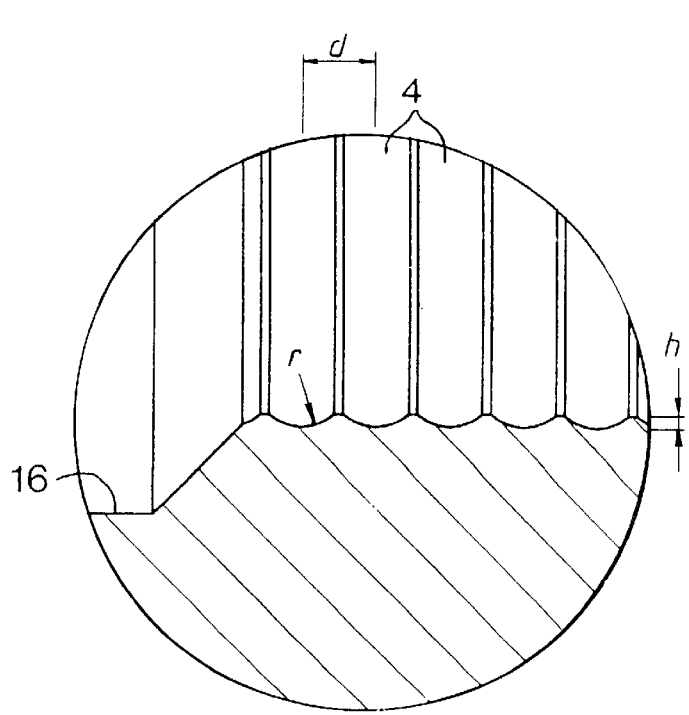
Figure 5:
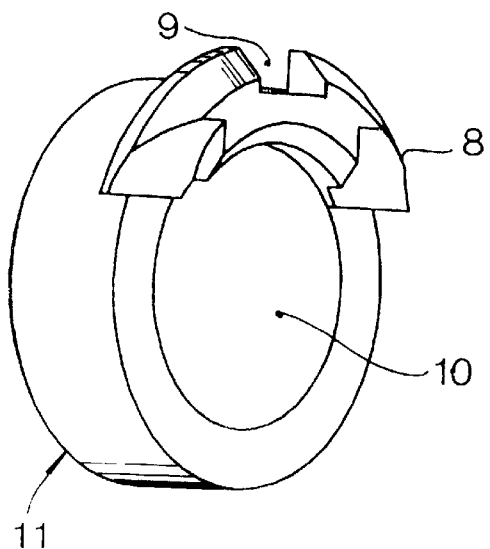
Figure 7:
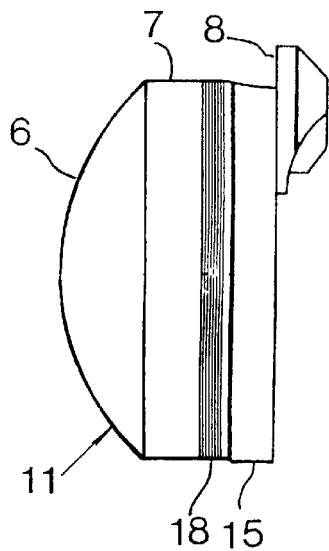
Figure 6:
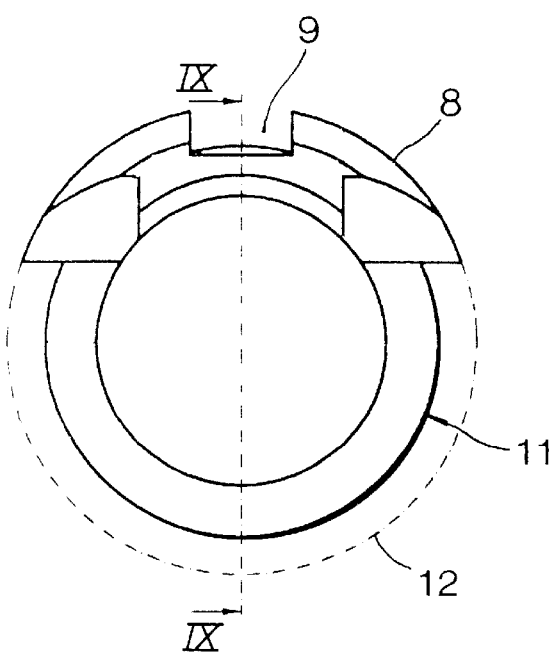
Figure 8:
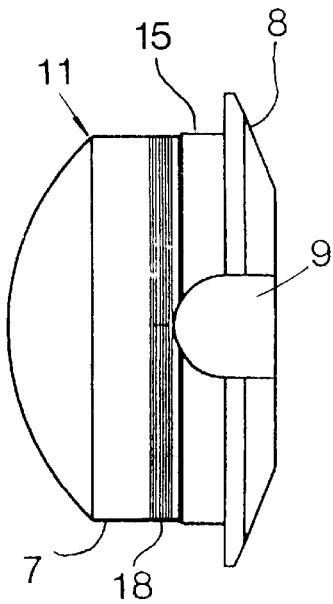
Figure 9:
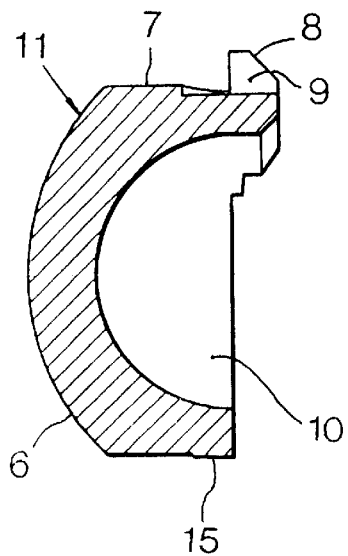

FIGS. 1 and 2 show an acetabular cup 1 according to a preferred embodiment of the invention. The cup, which is made of titanium, comprises a part 2 in the form of a spherical segment and a part 3 with a cylindrical inside. The inside of the part 3 is provided with a grooved region 4 providing retention means which in a preferred embodiment has been obtained by scoring the inside of the side wall with a suitable tool when turning the cup in a lathe. The score marks 4 are illustrated in FIG. 4 and, as seen in this figure, the tool used has a tip radius r which in this case is 0.1 mm, the feed being d=0.15 mm. The depth h of the scores is 0.025 mm. More conveniently, the turning and feeding operations may be performed simultaneously, resulting in a single helical groove having the same dimensions. The grooved part is located in the central part of the cylindrical part 3, the surface on both sides of the grooved part being smooth. The part 16 of the cylindrical part 3 located closest to the opening of the cup has a diameter which is about 0.4 mm larger than the diameter of the rest of the cylindrical part 3.

The free edge of the cup is provided with an axially oriented, projecting lug 5. The cup may be attached to the acetabulum according to any suitable standard procedure or by any suitable standard means.

A liner according to the invention is shown in FIGS. 5 to 10. The liner 11 has an outside shape which is complementary to the shape of the inside of the cup and consequently is provided with a part 6 having the shape of a spherical segment and a cylindrical part or sidewalls 7. The outermost part 15 of the sidewalls 7 of the liner has a slightly larger diameter than the remaining part of the sidewalls 7 in order to correspond to the part 16 in the cup. The edge of the liner is partly provided with a radially oriented peripheral flange 8 provided with a cut-out 9 corresponding to the lug 5. The cutout 9 is extended into the part 15. As indicated by means of the dotted line 12 in FIG. 6, the main portion of the flange 8, i.e. the part in use located at the lower and side portions of the liner, has been cut away in order to allow a free movement of the prosthesis in the liner, which is provided with a half-spherical cavity 10 adapted to receive an artificial, ballshaped femoral head. The diameter of the outer cylindrical part of the liner is equal to or a fraction smaller than the diameters of the cylindrical parts of the cup at room temperature. One reason for this is that the liner should be guided straight into the cup, minimizing the risk of the liner canting and consequently sticking during insertion. The liner is made of Ultra High Molecular Weight Polyethylene (UHMWPE).

The central part of the outer cylindrical part 7 of the liner is provided with a protruding, oriented grooved region 18, which in the preferred embodiment is in the form of thin, circumferential beads 13 separated by grooves 14. The area provided with beads is located to coincide with the grooved area on the inside of the cup when the liner is mounted in the cup. The remaining parts of the sidewalls of the liner are smooth.

Figure 10:
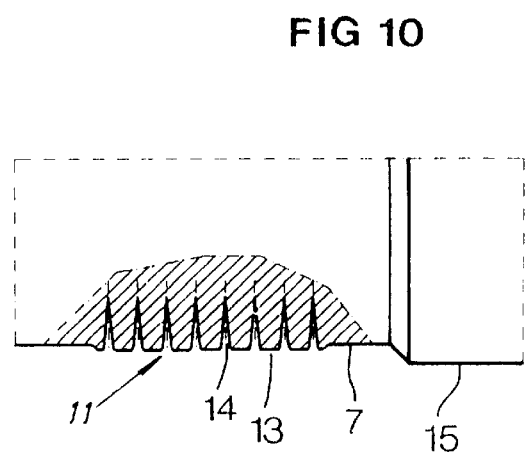
Figure 11:
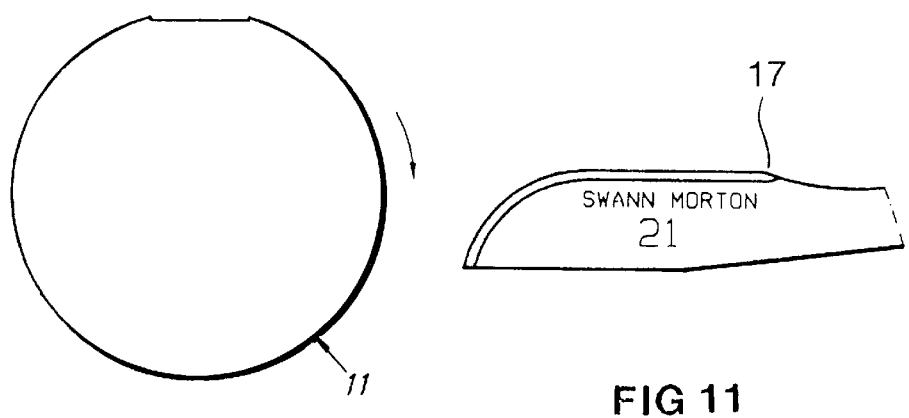

One method of making the beads on the surface of the liner is illustrated in FIG. 11. In this method 0.5 mm deep grooves are cut into the surface of the liner at a distance of 0.4 mm from each other by means of a cutting instrument 17 with a curved cutting edge, which here is illustrated by means of a standard scalpel blade, Swann Morton No. 21 (by which means a suitable cutting edge may be defined). Although different types of cutting edges could be used, it is advantageous to use a cutting edge having a tip of the cutting part which is tangential to the circumference of the liner during the cutting operation. During the cutting operation the liner is rotated and the cutting edge is held stationary against the side of the liner. The cutting operation will force the material in the areas between the cuts to expand outwardly to form circumferential beads projecting from the surface of the liner, as illustrated in FIG. 10. Since a cutting operation, not just a deforming operation, is performed in the polymeric material, the material will not flow back into the cuts and the beads will essentially keep their shape. The resulting beads will protrude a distance of about 0.10–0.14 mm from the surface of the liner.

When the cup-liner assembly is to be mounted in the acetabulum, the operation is begun by inserting and attaching the cup in a prepared cavity in the acetabulum in the way the cup is designed to be attached. The liner is then carefully slid into the cup, the beads 13 engaging with the cylindrical inner surface of the cup at the transitional zone between the outer part of the cup with a larger diameter and the inner cylindrical part. The provision of a outer cylindrical part with a larger diameter will permit the beads to move freely up to the transitional zone without engaging the inside of the cup. The tips of the beads will resiliently yield slightly outwardly, opposite to the direction of insertion at the transitional zone. Accommodation of the beads to the cup will be facilitated by means of the intermediate cuts 14.

When the liner is fully inserted, the tips of the beads will engage the circumferential grooves on the inside of the cup, still being oriented outwardly, thus effectively locking the liner in the cup. Normally this is sufficient to seal the interior of the cup-liner interface and also prevent the liner from moving relative to the cup as a result of the load variations in use. However, it is possible to choose the liner material so that, when the material of the liner is warmed from room temperature to body temperature, the smooth, cylindrical parts of the liner will expand slightly outwards against the corresponding, cylindrical parts of the inside of the cup.

The lug 5 and the cut-out 9 will aid in orienting the liner correctly and also hold the liner against rotation.

By the above means a surprisingly efficient way of attaching a liner into an acetabular cup is obtained and the resulting bond between cup and liner is strong and secure.

The invention may be varied in many ways within the scope of the appended claims. Although the design of the cooperating surfaces of liner and cup have been described as being cylindrical in the preferred embodiment, any design including opposing, substantially parallel or adapted surfaces would be suitable.

It should be noted that the outside of the cup does not form part of the invention and consequently may have any shape conducive to the attachment thereof into the acetabulum.

The height of the beads may vary between 0.08 and 1.0 mm, in a preferred embodiment between 0.1 and 0.7 mm, in another preferred embodiment 0.1 and 0.5 mm and in yet another preferred embodiment between 0.1 and 0.2 mm, the grooved region on the inside of the cup being adapted to these heights by having a slightly shallower depth.

The grooved region on the inside of the cup can be obtained in any suitable way, such as by blasting, by etching, by thread cutting, scoring or other ways of machining etc., and may of course also be production marks not removed by subsequent processing stages.

Likewise, the form, dimensions and production of the beads in the liner may take alternative embodiments such as angulated, unevenly spaced or directed or dimensioned cuts with or without gaps.

The beads on the liner may also be made by methods involving casting, turning, knurling, welding or other appropriate processes.

Of course, the beads may also be formed in parts projecting from the surface, for instance in a circumferential, elevated bands. This would be of particular relevance if the beads are formed by methods only entailing a removal of material such as turning, thread-cutting and similar or methods involving the use of laser beams oriented radially or axially relative to the cylindrical part of the cup.

The scored part is illustrated in as being located in the central part of the cooperating parts of the cylindrical parts of the cup-liner assembly, but may of course be located in other parts thereof.

We claim:

1. An acetabular cup-liner assembly comprising:
    an acetabular cup having an outer surface intended to face the bone tissue in the acetabulum and an inner surface; and
    a liner having an outer surface intended to face the inner surface of the cup;
    wherein the inner surface of the cup bounds a cavity having an opening adapted to receive said liner;
    wherein the outer surface of said liner and the inner surface of the cup are of complementary profile;
    wherein a section of the inner surface of the cup adjacent the opening is presented by a cylindrical inner side wall of the cup having inner dimensions and the liner has a corresponding outer side wall of dimensions equal to or a fraction less than the inner dimensions of said inner side wall whereby the cup-liner assembly is able to be assembled by translational movement of the liner into the cavity in the cup through the opening thereof;
    wherein the section of the inner surface presented by the inner side wall of said cup is provided with a preformed grooved region in the central part thereof to leave a smooth, cylindrical part on each side of said grooved region, said grooved region comprising a circumferentially oriented series of grooves or one or more helical grooves; and
    wherein said outer side wall of said liner is provided with a preformed grooved region for engagement with said preformed grooved region on said cup when assembled to secure the cup and liner together.

2. An acetabular cup-liner assembly comprising:

an acetabular cup having an outer surface intended to face the bone tissue in the acetabulum and an inner surface; and a liner having an outer surface intended to face the inner surface of the cup;

wherein the inner surface of the cup bounds a cavity having an opening adapted to receive said liner;

wherein the outer surface of said liner and the inner surface of the cup are of complementary profile;

wherein the inner surface of the cup has parts adjacent the cup opening which are presented by an inner side wall of the cup having inner dimensions and the liner has a corresponding outer side wall having dimensions equal to or a fraction less than the inner dimensions of said inner side wall whereby the cup-liner assembly is able to be assembled by translational movement of the liner into the cavity in the cup through the opening thereof;

wherein the parts of the inner surface of the cup located adjacent to said opening presented by the inner side wall are essentially parallel to each other and provided with a preformed grooved region; and wherein said outer side wall of the liner is provided with a preformed grooved region for engagement with the preformed grooved region on the inner side wall of the cup when the cup and liner are assembled, the preformed grooved region on the liner being in the form of circumferential beads separated by grooves with the bead tips adapted to engage with the preformed grooved region on the cup and incline towards the cup opening to secure the cup and liner together.

3. An assembly as claimed in claim 2 in which the inner side wall of the cup is cylindrical.

4. An assembly as claimed in claim 1 or 2 in which the grooved region on the cup comprises one or more grooves obtained by scoring said surface in a turning operation, and the depth of said grooves is between 0.020 and 0.30 mm.

5. An assembly as claimed in claim 4 in which the distance between adjacent grooves is between 0.12 and 0.2 mm.

6. An assembly as claimed in claim 1 or 2 in which said grooved region on the liner defines a series of beads extending approximately 0.08–1.0 mm from the outer side wall of the liner.

7. An assembly as claimed in claim 1 in which said preformed grooved region on the outer side wall of the liner is in the form of circumferential beads separated by grooves with the beads tips adapted to engage with the preformed grooved region on the cup and incline towards the cup opening on insertion of the liner into the cup.

8. An assembly as claimed in claim 2 in which the preformed grooved region on the cup is located in a central part of the inner side wall to leave a smooth, cylindrical part on each side of said grooved region.

9. An assembly as claimed in claim 2 in which said preformed grooved region on the cup comprises a circumferentially oriented series of grooves or one or more helical grooves.

10. A method of providing a grooved region comprising a circumferentially oriented series of grooves or one or more helical grooves on the cylindrical inner side wall of an acetabular cup for use in an assembly as claimed in claim 1 or claim 3, comprising the step of scoring the cylindrical inner side wall in a turning operation.

11. A method as claimed in claim 10 in which the scoring is carried out with a tool having a specified tip radius and operating with a specified feed.

12. A method as claimed in claim 11 in which said tool has a tip radius of 0.1 mm, and the feed is 0.15 mm resulting in the scores having a depth of 0.025 mm.

13. A method of providing a grooved region comprising inclinable circumferential beads separated by grooves on the outer side wall of a liner for use in an assembly as claimed in claim 6, comprising the step of cutting the outer side wall of the liner with a sharp-edged tool in a turning operation.

14. A method as claimed in claim 13 in which said grooves are cut to a depth of approximately 0.5 mm, the distance between each groove being approximately 0.4 mm.

* * * * *